United States Patent
Chen et al.

(10) Patent No.: US 9,815,801 B2
(45) Date of Patent: Nov. 14, 2017

(54) METHOD OF REFINING VALSARTAN COMPRISING MORE THAN OR EQUAL TO 10% D-ISOMERS

(71) Applicant: ZHEJIANG HUAHAI PHARMACEUTICAL CO., LTD, Taizhou, Zhejiang (CN)

(72) Inventors: Yongbi Chen, Taizhou (CN); Wenling Zhang, Taizhou (CN); Peng Wang, Taizhou (CN); Jian Chen, Taizhou (CN)

(73) Assignee: ZHEJIANG HUAHAI PHARMACEUTICAL CO., LTD., Taizhou (CN)

( * ) Notice: Subject to any disclaimer, the term of this patent is extended or adjusted under 35 U.S.C. 154(b) by 0 days.

(21) Appl. No.: 15/108,209

(22) PCT Filed: Feb. 15, 2015

(86) PCT No.: PCT/CN2015/073126
§ 371 (c)(1),
(2) Date: Jun. 24, 2016

(87) PCT Pub. No.: WO2015/124102
PCT Pub. Date: Aug. 27, 2015

(65) Prior Publication Data
US 2016/0347723 A1    Dec. 1, 2016

(30) Foreign Application Priority Data

Feb. 21, 2014 (CN) .......................... 2014 1 0063384

(51) Int. Cl.
*C07D 257/04* (2006.01)

(52) U.S. Cl.
CPC ........ *C07D 257/04* (2013.01); *C07B 2200/09* (2013.01)

(58) Field of Classification Search
CPC .................................................. C07D 257/04
See application file for complete search history.

(56) References Cited

FOREIGN PATENT DOCUMENTS

| CN | 101768128 A | * | 7/2010 |
|---|---|---|---|
| CN | 102617497 A | | 8/2012 |
| CN | 103819421 A | | 5/2014 |
| WO | 2007069271 A2 | | 6/2007 |

OTHER PUBLICATIONS

Machine translation of CN 102617497, obtained from espacenet on Mar. 2, 2017.*
Kumar et al., "New and Improved Manufacturing Process for Valsartan" Organic Process Res. & Dev., 13:1185-1189, 2009.

* cited by examiner

*Primary Examiner* — Matthew Coughlin
(74) *Attorney, Agent, or Firm* — McCarter & English, LLP; Steven G. Davis; Mei Bai

(57) ABSTRACT

The present invention relates to a method of refining valsartan comprising more than or equal to 10% D-isomers, the method comprising: adding a solvent to valsartan comprising more than or equal to 10% D-isomers to dissolve it, then adding a certain amount of inorganic base, separating solids out after salification, distilling a filtrate after filtration, and distilling the filtrate to remove the organic solvent; adjusting the pH of the filtrate with an acid, extracting with an organic solvent, concentrating most of the organic solvent, cooling to crystallize, and obtaining the product. The method enables isomers of the product to be below 0.5%, and produce a yield of more than or equal to 40%, being suitable for industrial production.

19 Claims, No Drawings

METHOD OF REFINING VALSARTAN COMPRISING MORE THAN OR EQUAL TO 10% D-ISOMERS

RELATED APPLICATION

The present application is a U.S. National Stage application filed under 35 U.S.C. § 371, based on International Application No. PCT/CN2015/073126, titled "METHOD OF REFINING VALSARTAN COMPRISING MORE THAN 10% D-ISOMERS," filed on Feb. 15, 2015, which claims the priority of Chinese Patent Application No. 201410063384.1, titled "METHOD OF REFINING VALSARTAN COMPRISING MORE THAN 10% D-ISOMERS," filed on Feb. 21, 2014, the content of each of which is hereby incorporated into the present application by reference in its entirety.

FIELD OF INVENTION

The present application relates to the field of pharmaceutical chemical industry, and in particular to a method of refining valsartan comprising more than or equal to 10% D-isomers.

BACKGROUND OF THE INVENTION

Valsartan is an orally effective and specific angiotensin II (AT1) receptor antagonist, the chemical name of which is N-(1-valeryl)-N-[4-[2-(1H-tetrazolium-5-yl)phenyl]benzyl]-L-valine. Valsartan acts on AT1 receptor subtype selectively and blocks the combination of Ang II and AT1 receptor (the specific antagonism on AT1 receptor is about 30,000 times greater than that on AT2 receptor), to inhibit vasoconstriction and the release of aldosterone, achieving an antihypertensive effect.

During synthesis process, under the influence of the reaction conditions, a portion of valsartan products will be racemized to obtain D isomer of valsartan which is not pharmaceutically eligible. Valsartan comprising fewer isomers is obtained by crystallization in production. Meanwhile, the content of isomers in the mother liquor reaches more than or equal to 10%, even more than or equal to 20%, or yet even more than or equal to 30% (measured by HPLC area normalization method) after crystallization. Currently, no literature discloses a method excellent in recovering valsartan of pharmaceutically eligible configuration from the mother liquor with such a high content of isomers.

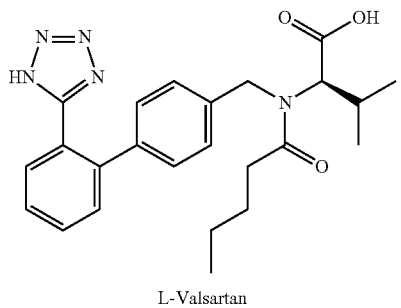

L-Valsartan

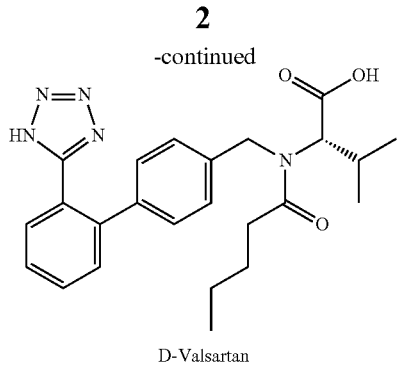

D-Valsartan

SUMMARY OF THE INVENTION

The object of the present application is to provide a method of refining valsartan comprising more than or equal to 10%, even more than or equal to 20%, or yet even more than or equal to 30% D-isomers, the method comprising the following steps:

1) adding a solvent to valsartan comprising more than or equal to 10% D-isomers to dissolve it, then adding a certain amount of inorganic base, separating solids out after salification, obtaining a filtrate after filtration, and distilling the filtrate to remove the organic solvent; and 2) adjusting the pH of the filtrate with an acid, extracting with an organic solvent, concentrating most of the organic solvent, cooling to crystallize, and obtaining the product.

In the method, the solvent used in step 1) is selected from any one of acetonitrile/water, butanone/water, acetone/water, methanol/water, or tetrahydrofuran/water, and preferably any one of methanol/water, tetrahydrofuran/water, and butanone/water. The inorganic base used is selected from any one of NaOH, KOH, LiOH.$H_2O$, Ba(OH)$_2$.8$H_2O$, and Ca(OH)$_2$, or any combination thereof. As known for those skilled in the art, the inorganic base used is not limited thereto, and the inorganic bases can be used as long as they can realize the present invention.

The ratio of the solvent used in step 1) to valsartan is 1.0~8.0 ml/g, preferably 1.0~5.0 ml/g, and more preferably 1.0~3.0 ml/g. The molar ratio of the inorganic base used to valsartan is 1.1~5, preferably 1.1~3.0, and more preferably 1.1~1.8. The ratio of water in the mixed solvent to valsartan is 1.0~10.0 ml/g, preferably 2.0~10.0 mg/g, more preferably 1.0~5.0 ml/g, and even more preferably 1.0~2.0 ml/g. The inventor discovers that it is advantageous for the reaction system to carry out the present invention within the aforementioned preferable ranges.

The acid used in step 2) of the method can be any inorganic acid or organic acid. That is, the acid can be selected from any one of an inorganic acid such as hydrochloric acid, sulfuric acid, nitric acid, phosphoric acid, and the like, and an organic acid such as methanoic acid, acetic acid, oxalic acid, and the like, or any combination thereof. The organic solvent used is any one of ethyl acetate, toluene, and dichloromethane, or any combination thereof.

In step 2), the pH is adjusted to 0.5~4.0.

The refining method provided by the present invention has an advantage of reducing D-isomers significantly. D-isomers can be reduced to less than or equal to 0.5% effectively with one refining. And the yield reaches more than or equal to 40% with low recovery cost. It is most important to allow recovering valsartan of pharmaceutically eligible configuration from valsartan with a high content of isomers.

Surprisingly, the inventor discovers that the method of the present invention can be used to refine valsartan comprising more than or equal to 10%, even more than or equal to 20%, or yet even more than or equal to 30% D-isomers, and the content of D-isomers can be reduced to less than or equal to 0.5%. Meanwhile, the method of the present invention is easy to operate, environment friendly, and appropriate for industrial production.

DETAILED DESCRIPTION OF THE INVENTION

The present invention will be described in detail from the following examples. However, these examples are not intended to limit the invention in any manner.

EXAMPLE 1

15 g valsartan comprising 22% isomers was added into a 50 ml single-neck flask, 30 ml acetonitrile was added, and the mixture was stirred until clarification and left for later.

2 g NaOH and 40 ml water were added into a 250 ml four-neck flask and stirred until clarification. The solution of valsartan in acetonitrile prepared above was added dropwise. The resulting solution was cooled down to 0° C., stirred, crystallized for 8 hours, and then filtered with suction. The filtrate was distilled under reduced pressure to remove the organic solvent. 6 N hydrochloric acid was added to adjust the pH to 2.0. The filtrate was extracted with 50 ml ethyl acetate, dried with anhydrous magnesium sulfate, filtered to remove the solid, concentrated to remove 10 ml ethyl acetate, cooled down to −5° C., stirred and crystallized for 12 hours, filtered, and dried, affording 7.1 g solid. The yield was 47%, and the content of isomers was determined to be 0.46%.

EXAMPLE 2

15 g valsartan comprising 19% isomers was added into a 50 ml single-neck flask, 40 ml butanone was added, and the mixture was stirred until clarification and left for later.

2.3 g KOH and 60 ml water were added into a 250 ml four-neck flask and stirred until clarification. The solution of valsartan in butanone prepared above was added dropwise. The resulting solution was cooled down to 0° C., stirred and crystallized for 8 hours, and then filtered with suction. The filtrate was distilled under reduced pressure to remove the organic solvent. Oxalic acid was added to adjust the pH to 0.5. The filtrate was extracted with 50 ml toluene, dried with anhydrous magnesium sulfate, filtered to remove the solid, concentrated to remove 10 ml toluene, cooled down to −5° C., stirred and crystallized for 12 hours, filtered, and dried, affording 5.3 g solid. The yield was 35%, and the content of isomers was determined to be 0.45%.

EXAMPLE 3

15 g valsartan comprising 31% isomers was added into a 50 ml single-neck flask, 25 ml acetone was added, and the mixture was stirred until clarification and left for later. 2.2 g $LiOH.H_2O$ and 70 ml water were added into a 250 ml four-neck flask and stirred until clarification. The solution of valsartan in acetone prepared above was added dropwise. The resulting solution was cooled down to 0° C., stirred and crystallized for 8 hours, and then filtered with suction. The filtrate was distilled under reduced pressure to remove the organic solvent. 20% sulfuric acid was added to adjust the pH to 3.0. The filtrate was extracted with 70 ml dichloromethane, dried with anhydrous magnesium sulfate, filtered to remove the solid, concentrated to remove 40 ml dichloromethane, cooled down to −5° C., stirred and crystallized for 12 hours, filtered, and dried, affording 6.2 g solid. The yield was 41%, and the content of isomers was determined to be 0.46%.

EXAMPLE 4

15 g valsartan comprising 19% isomers was added into a 50 ml single-neck flask, 20 ml methanol was added, and the mixture was stirred until clarification and left for later. 4.2 g $Ca(OH)_2$ and 90 ml water were added into a 250 ml four-neck flask and stirred until clarification. The solution of valsartan in methanol prepared above was added dropwise. The resulting solution was cooled down to 0° C., stirred and crystallized for 8 hours, and then filtered with suction. The filtrate was distilled under reduced pressure to remove the organic solvent. 4 N nitric acid was added to adjust the pH to 1.5. The filtrate was extracted with 50 ml toluene, dried with anhydrous magnesium sulfate, filtered to remove the solid, concentrated to remove 10 ml toluene, cooled down to −5° C., stirred and crystallized for 12 hours, filtered, and dried, affording 6.0 g solid. The yield was 40%, and the content of isomers was determined to be 0.39%.

EXAMPLE 5

15 g valsartan comprising 28% isomers was added into a 50 ml single-neck flask, 30 ml tetrahydrofuran was added, and the mixture was stirred until clarification and left for later. 7.9 g $Ba(OH)_2.8H_2O$ and 75 ml water were added into a 250 ml four-neck flask and stirred until clarification. The solution of valsartan in tetrahydrofuran prepared above was added dropwise. The resulting solution was cooled down to 0° C., stirred and crystallized for 8 hours, and then filtered with suction. The filtrate was distilled under reduced pressure to remove the organic solvent. Methanoic acid was added to adjust the pH to 2.5. The filtrate was extracted with 80 ml dichloromethane, dried with anhydrous magnesium sulfate, filtered to remove the solid, concentrated to remove 40 ml dichloromethane, cooled down to −5° C., stirred and crystallized for 12 hours, filtered, and dried, affording 6.3 g solid. The yield was 42%, and the content of isomers was determined to be 0.37%.

EXAMPLE 6

15 g valsartan comprising 37% isomers was added into a 50 ml single-neck flask , 20 ml butanone was added, and the mixture was stirred until clarification and left for later.

2.3 g KOH and 60 ml water were added into a 250 ml four-neck flask of and stirred until clarification. The solution of valsartan in butanone prepared above was added dropwise. The resulting solution was cooled down to 0° C., stirred and crystallized for 8 hours, and then filtered with suction. The filtrate was distilled under reduced pressure to remove the organic solvent. 20% phosphoric acid was added to adjust the pH to 1.5. The filtrate was extracted with 75 ml toluene, dried with anhydrous magnesium sulfate, filtered to remove the solid, concentrated to remove 40 ml toluene, cooled down to −5° C., stirred and crystallized for 12 hours, filtered, and dried, affording 3.5 g solid. The yield was 23%, and the content of isomers was determined to be 0.35%.

EXAMPLE 7

15 g valsartan comprising 19% isomers was added into a 50 ml single-neck flask, 25 ml methanol was added, and the mixture was stirred until clarification and left for later.

2.2 g LiOH.H$_2$O and 30 ml water were added into a 250 ml four-neck flask and stirred until clarification. The solution of valsartan in methanol prepared above was added dropwise. The resulting solution was cooled down to 0° C., stirred and crystallized for 8 hours, and then filtered with suction. The filtrate was distilled under reduced pressure to remove the organic solvent. Oxalic acid was added to adjust the pH to 4.0. The filtrate was extracted with 70 ml dichloromethane, dried over anhydrous magnesium sulfate, filtered to remove the solid, concentrated to remove 30 ml dichloromethane, cooled down to −5° C., stirred and crystallized for 12 hours, filtered, and dried, affording 6.6 g solid. The yield was 44%, and the content of isomers was determined to be 0.43%.

The foregoings are only preferred examples of the present invention, and are not intended to limit the present invention. Any modifications, equivalent replacements, improvements and the like within the spirit and principle of the present invention shall fall into the protection scope of the present invention.

COMPARATIVE EXAMPLE 1

The Method of Refining Valsartan According to Prior Art 10 g valsartan comprising 19% isomers was added into a 50 ml single-neck flask, 16 g ethanol was then added, and the mixture was stirred to dissolve valsartan at 20° C. After dissolution, 4 g calcium hydroxide was added. The resulting solution was stirred for 2 hours at 20° C. and filtered, affording a calcium salt of valsartan. The calcium salt of valsartan was added into a 250 ml beaker, 45 g ethyl acetate was added, and aqueous solution of diluted hydrochloric acid with a mass percentage concentration of 9% was further added to adjust the pH to 2. After adjustment, the system was separated into different layers. The ester solvent layer was washed twice with water, and dried under reduced pressure to recover anhydrous solvent. The residue is solubilized with 43 g ethyl acetate. After solubilization, the resulting solution was stirred, crystallized, slowly cooled down to −2.5° C.±2.5° C., centrifuged, and drying under reduced pressure, affording 7.0 g valsartan. The yield was 70%, and the content of chiral isomers was determined to be 18%.

The above procedures were repeated on the obtained valsartan comprising 18% isomers, affording 4.0 g valsartan. The yield was 57.1%, and the content of chiral isomers was determined to be 17%.

The above procedures were repeated for another time on the obtained valsartan comprising 17% isomers, affording 2.0 g valsartan. The yield was 50%, and the content of chiral isomers was determined to be 16%.

According to the method of refining valsartan in prior art, the total yield decreased down to 20% after repeating the procedures three times, while the content of chiral isomers was still up to 16%. Thus, the method according to prior art cannot realize the refining of valsartan comprising more than or equal to 10% D-isomers.

What is claimed is:

1. A method of refining valsartan comprising more than or equal to 10% D-isomers, characterized in that the method comprises the following steps:

1) adding a solvent to valsartan comprising more than or equal to 10% D-isomers to dissolve it, then adding a certain amount of inorganic base, separating solids out after salification, obtaining a filtrate after filtration, and distilling the filtrate to remove the solvent; and 2) adjusting the pH of the filtrate with an acid, extracting with an organic solvent, concentrating most of the organic solvent, cooling to crystallize, and obtaining the product.

2. The method of refining valsartan comprising more than or equal to 10% D-isomers according to claim 1, characterized in that the solvent used in step 1) is a mixed solvent of water and a solvent selected from acetonitrile, butanone, acetone, methanol, or tetrahydrofuran.

3. The method of refining valsartan comprising more than or equal to 10% D-isomers according to claim 1, characterized in that the inorganic base used in step 1) is selected from any one of NaOH, KOH, LiOH.H$_2$O, Ba(OH)$_2$.8H$_2$O, and Ca(OH)$_2$, or any combination thereof.

4. The method of refining valsartan comprising more than or equal to 10% D-isomers according to claim 1, characterized in that the ratio of the solvent used in step 1) to valsartan is 1.0-8.0 ml/g.

5. The method of refining valsartan comprising more than or equal to 10% D-isomers according to claim 1, characterized in that the molar ratio of the inorganic base used in step 1) to valsartan is 1.1-5.

6. The method of refining valsartan comprising more than or equal to 10% D-isomers according to claim 2, characterized in that the ratio of water in the solvent used in step 1) to valsartan is 1.0-10.0 ml/g.

7. The method of refining valsartan comprising more than or equal to 10% D-isomers according to claim 1, characterized in that the acid used in step 2) is selected from any one of hydrochloric acid, sulfuric acid, nitric acid, phosphoric acid, methanoic acid, acetic acid, and oxalic acid, or any combination thereof.

8. The method of refining valsartan comprising more than or equal to 10% D-isomers according to claim 1, characterized in that in step 2) the pH is adjusted to 0.5 -4.0.

9. The method of refining valsartan comprising more than or equal to 10% D-isomers according to claim 1, characterized in that the organic solvent used in step 2) is any one of ethyl acetate, toluene, and dichloromethane, or any combination thereof.

10. The method of refining valsartan comprising more than or equal to 10% D-isomers according to claim 2, characterized in that the solvent used in step 1) is any one of methanol/water, tetrahydrofuran/water, and butanone/water.

11. The method of refining valsartan comprising more than or equal to 10% D-isomers according to claim 4, characterized in that the ratio of the solvent used in step 1) to valsartan is 1.0-5.0 ml/g.

12. The method of refining valsartan comprising more than or equal to 10% D-isomers according to claim 4, characterized in that the ratio of the solvent used in step 1) to valsartan is 1.0-3.0 ml/g.

13. The method of refining valsartan comprising more than or equal to 10% D-isomers according to claim 5, characterized in that the molar ratio of the inorganic base used in step 1) to valsartan is 1.1-3.0.

14. The method of refining valsartan comprising more than or equal to 10% D-isomers according to claim 5, characterized in that the molar ratio of the inorganic base used in step 1) to valsartan is 1.1-1.8.

15. The method of refining valsartan comprising more than or equal to 10% D-isomers according to claim 6, characterized in that the ratio of water in the solvent used in step 1) to valsartan is 2.0-10.0 ml/g.

16. The method of refining valsartan comprising more than or equal to 10% D-isomers according to claim 6, characterized in that the ratio of water in the solvent used in step 1) to valsartan is 1.0-5.0 ml/g.

17. The method of refining valsartan comprising more than or equal to 10% D-isomers according to claim 6, characterized in that the ratio of water in the solvent used in step 1) to valsartan is 1.0-2.0 ml/g.

18. The method of refining valsartan comprising more than or equal to 10% D-isomers according to claim 1, characterized in that the valsartan comprises more than or equal to 20% D-isomers.

19. The method of refining valsartan comprising more than or equal to 10% D-isomers according to claim 1, characterized in that the valsartan comprises more than or equal to 30% D-isomers.

* * * * *